(12) United States Patent
Ruch et al.

(10) Patent No.: US 11,406,299 B2
(45) Date of Patent: Aug. 9, 2022

(54) BIOSENSORS WITH PROGRAMMABLE SENSING CAVITIES

(71) Applicant: International Business Machines Corporation, Armonk, NY (US)

(72) Inventors: Patrick Ruch, Pratval (CH); Jonas Weiss, Oberrieden (CH)

(73) Assignee: International Business Machines Corporation, Armonk, NY (US)

(*) Notice: Subject to any disclaimer, the term of this patent is extended or adjusted under 35 U.S.C. 154(b) by 840 days.

(21) Appl. No.: 16/282,543

(22) Filed: Feb. 22, 2019

(65) Prior Publication Data
US 2020/0268289 A1 Aug. 27, 2020

(51) Int. Cl.
*A61B 5/1468* (2006.01)
*B01L 3/00* (2006.01)
(Continued)

(52) U.S. Cl.
CPC .......... *A61B 5/1468* (2013.01); *A61B 5/1486* (2013.01); *B01L 3/5027* (2013.01);
(Continued)

(58) Field of Classification Search
CPC . A61B 5/1468; A61B 5/1486; A61B 5/14552; A61B 5/6801; A61B 5/14532; A61B 2562/12; B01L 3/5027; B01L 3/502715; B01L 3/50823; B01L 2300/0645; B01L 2400/0677; G01N 33/5438; G01N 27/27; G01N 27/327; G01N 27/403
See application file for complete search history.

(56) References Cited

U.S. PATENT DOCUMENTS 5,827,948 A   10/1998  Martell et al.
7,019,305 B2   3/2006  Eversmann et al.
(Continued)

FOREIGN PATENT DOCUMENTS

CN   102395879 A    3/2020
KR   2015-0113350  10/2015
WO   2018/130694 A2  7/2018

OTHER PUBLICATIONS

United Kingdom Examination Report dated Apr. 7, 2022 received in Application No. GB2113184.2, 3 pages.
(Continued)

*Primary Examiner* — Jennifer Wecker
*Assistant Examiner* — Alea N. Martin
(74) *Attorney, Agent, or Firm* — Scully, Scott, Murphy & Presser, P.C.; Daniel P. Morris (57) ABSTRACT

A sensor comprises a microfabricated chip having a surface with one or more cavities formed thereon, the cavities including sensing components, one or more lids, each covering said surface so as to close at least one of said cavities, the lids contacting rims that delimit said cavities on said surface. Electric circuit portions join, each, a respective one of the lids, to allow the lids to be partly dissolved, electrochemically, responsive to being exposed to an electrochemical solution. In addition, masking material portions cover peripheral regions of the lids at the level of the rims, so as to seal the lids and shield such peripheral regions from said electrochemical solution, in operation. Related apparatuses and sensing methods may be provided.

20 Claims, 6 Drawing Sheets

(51) Int. Cl.
  *G01N 33/543*  (2006.01)
  *A61B 5/1455*  (2006.01)
  *A61B 5/1486*  (2006.01)
  *A61B 5/00*    (2006.01)

(52) U.S. Cl.
  CPC ...... *G01N 33/5438* (2013.01); *A61B 5/14552* (2013.01); *A61B 5/6801* (2013.01)

(56) References Cited

U.S. PATENT DOCUMENTS

| | | |
|---|---|---|
| 8,523,773 B2 | 9/2013 | Shah et al. |
| 9,636,058 B2 | 5/2017 | Van Kesteren et al. |
| 2005/0006234 A1 | 1/2005 | Hassibi |
| 2005/0247559 A1 | 11/2005 | Frey et al. |
| 2010/0197524 A1 | 8/2010 | Janata et al. |
| 2013/0320476 A1* | 12/2013 | Jain .................... A61B 5/0017 257/434 |
| 2017/0172470 A1 | 6/2017 | Begtrup et al. |

OTHER PUBLICATIONS

International Search Report dated May 21, 2020, issued in PCT/IB2020/050695, 3 pages.

* cited by examiner

BIOSENSORS WITH PROGRAMMABLE SENSING CAVITIES

BACKGROUND

The present disclosure in general to the fields of sensors, sensing apparatuses and method, and, in particular to biosensors. The present disclosure is directed to a biosensor comprising cavities with electrodes and bioreceptors arranged therein, where the cavities are closed by lids which can be programmatically dissolved, electrochemically, to expose the cavities for sensing purposes.

Electrochemical biosensors are widely used to detect analytes in biological systems, such as glucose in blood. Such sensors can for instance be implemented in point-of-care diagnostics (POCDs) or used for environmental analysis and drug discovery purposes. POCDs strongly benefit from miniaturization, which enhances portability and the integration of various functions into one diagnostic device.

Figure 1:
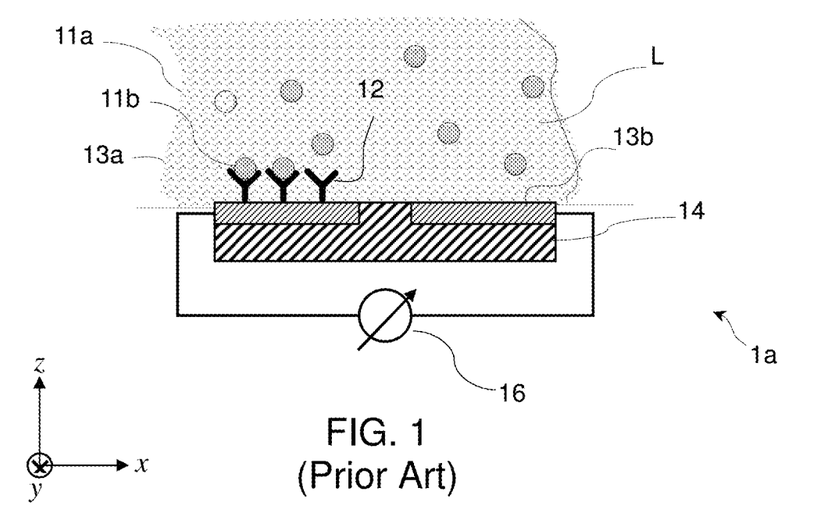
FIG. 1 is a 2-dimensional (2D) cross-sectional view of a biosensor device, according to a known prior art approach.

An element of a biosensor is the bioreceptor, which is a biologically-derived material or a synthetic biomimetic material that interacts specifically with an analyte of interest. Such a bioreceptor limits the usability of conventional biosensors, inasmuch as it typically binds irreversibly with the analyte; the device can thus be used only once. In addition, bioreceptors typically limit the shelf life of a biosensor, for example due to oxidation in air or exposure to humidity. An example of such a biosensor $1a$ is sketched in FIG. 1, which shows a substrate 14, with built-in electrodes $13a$, $13b$, wherein one electrode $13a$ is covered with biosensors 12. Once exposed to a liquid L with analytes $11a$, some of the analytes $11b$ bind to the receptors 12, which yields a measurable signal on a readout device 16. This device $1a$ can only be used once with nominal sensitivity.

More sophisticated devices have been proposed. However, a limitation of such POCD devices is the lack of flexibility in defining/changing the assay conditions "on the fly", i.e., shortly before using them or during operations, because flow paths are typically encoded on a design level and set during microfabrication. This translates into devices that must be operated according to well-defined protocols and where flow rates and volumes of displaced liquids cannot easily be changed during operation without using active micro-components.

SUMMARY

According to a first aspect, the present invention is embodied as a sensor. The sensor comprises a microfabricated chip having a surface with one or more cavities formed thereon (the cavities including sensing components), as well as one or more lids, each covering said surface so as to close at least one of said cavities. The lids are in contact with rims that delimit said cavities on said surface. Electric circuit portions join, each, a respective one of the lids, to allow the lids to be partly dissolved, electrochemically, when exposed to an electrochemical solution. In addition, masking material portions cover peripheral regions of the lids at the level of the rims, so as to seal the lids and shield such peripheral regions from said electrochemical solution, in operation.

The sensing components can comprise, each, one or more electrodes arranged in a respective one of the cavities, and receptors anchored to said electrode(s). In that case, the sensor further includes second electric circuit portions connected to said electrodes.

According to another aspect, the invention is embodied as a sensing apparatus, which comprises a microfabricated chip such as described above. In addition, the apparatus comprises electrical control means, connected to electric circuit portions on the chip to allow the lids to be partly dissolved, electrochemically, when exposed to an electrochemical solution, in operation.

According to another aspect, the invention is embodied as a sensing method, which relies on a sensor or a sensing apparatus as described above. According to this method, the surface of the chip is first exposed to an electrochemical solution, and the electric circuit portions connecting one of the lids are energized to electrochemically dissolve an inner region of this lid, its peripheral regions being shielded from said electrochemical solution by one or more of the masking portions. This allows one or more sensing components to be exposed to an external medium. The latter is subsequently sensed via the exposed sensing components, e.g., via electrodes and (bio)receptors.

Sensor devices, in particular biosensors, apparatuses, and sensing methods embodying the present invention will now be described, by way of non-limiting examples, and in reference to the accompanying drawings.

BRIEF DESCRIPTION OF SEVERAL VIEWS OF THE DRAWINGS

The accompanying figures, where like reference numerals refer to identical or functionally similar elements throughout the separate views, and which together with the detailed description below are incorporated in and form part of the present specification, serve to further illustrate various embodiments and to explain various principles and advantages all in accordance with the present disclosure, in which.

The accompanying drawings show simplified representations of devices or parts thereof, as involved in embodiments. Technical features depicted in the drawings are not necessarily to scale. Similar or functionally similar elements in the figures have been allocated the same numeral references, unless otherwise indicated.

DETAILED DESCRIPTION OF EMBODIMENTS OF THE INVENTION

In one aspect, more flexible POCDs, biosensors, and, more generally, sensors may be provided. In one aspect, a type of sensors may be provided, relying on micro-structured chips with lids that can be programmatically dissolved. In one aspect, a biosensor device with bioreceptors may be provided that can be used several times and has a substantially longer shelf life. In one aspect, a biosensor device may be provided that can be programmed to conduct a series of biosensing experiments, following a logical sequence (e.g., encoded in a non-volatile memory), as discussed in the following description.

Note, in the present description, a sensor, or a sensor device, refers to a device that includes a microfabricated chip, and is typically a portable, integral device, which is designed so as to allow an external medium L to be sensed via sensing components of the device. Such a device may or may not include electronic peripherals to control the dissolution of the lids and read out measurement signals (for sensing purposes). On the contrary, a sensing apparatus is, in the present description, meant to include one or more of such peripheral devices, in addition to the sensor device. Such an apparatus may thus consist of several parts, which electrically connect to each other. Such parts may for instance be provided as a kit of parts, which may possibly assemble to form an integral device. The sensing methods described herein rely on such sensing devices and apparatuses.

In reference to FIGS. 2-4A-D, an aspect of the invention is first described, which concerns a sensor 1, 10. The sensor comprises a microfabricated chip 10. The chip exhibits a main surface S, e.g., a top surface, whereon one or more cavities 20 are formed. The device preferably includes several cavities 20, as assumed in the accompanying drawings and in the following description, for the sake of illustration. The cavities include, each, one or more sensing components 12, 13a, 13b.

In one aspect, the cavities are hollow cavities, e.g., formed as depressions formed on the surface S, such as grooves or notches (as assumed in the accompanying drawings), or by means of microstructures patterned on the surface (such as pillars and lids, not shown). The cavities 20 may for example be arranged in an array on said surface S, as exemplified in FIGS. 3A-3B. Note, such cavities may have a more sophisticated geometry than shown in the accompanying drawings. Some of the cavities may further be fluidly interconnected, e.g., by microchannels, if necessary.

The device 1 further includes lids 21 that cover, each, the surface S (partly), so as to close at least one respective cavity 20. The lids 21 are in mechanical contact with rims 20r on the surface S, where such rims 20r delimit the cavities formed on the surface S. The lids 21 are thin membranes (i.e., films) that tent over one or more cavities on the surface S. Each lid may for example tent over a single cavity 20, so as to close an aperture of the cavity at an upper level of the structured surface S. In variants, a lid 21 may possibly cover two or more cavities 20 and thus close several cavities, as assumed in FIG. 3A.

Figure 4A:
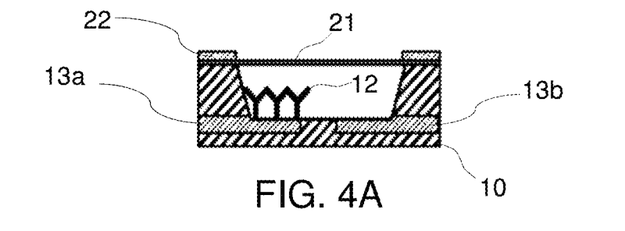
FIGS. 4A-4D show a sequence of 2D cross-sectional views illustrating basic steps of a sensing method that involves a sensor device such as depicted in FIG. 2, according to embodiments.
Figure 4B:
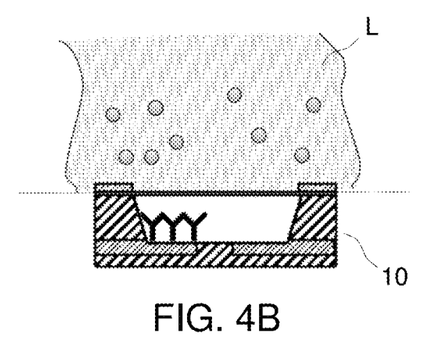
Figure 4C:
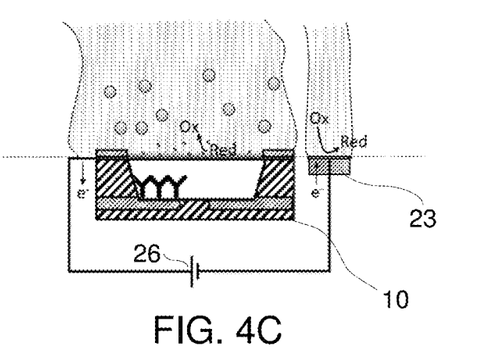
Figure 4D:
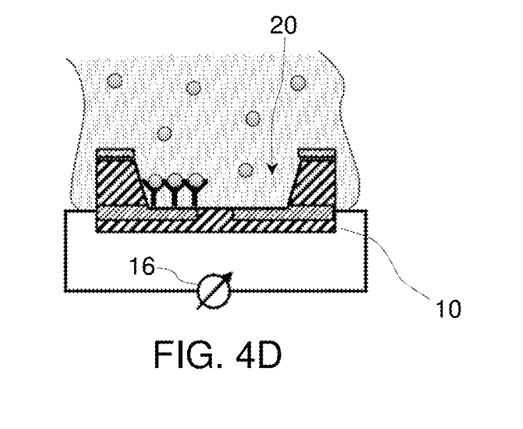

In addition, the device comprises electric circuit portions 25, e.g., formed as electrical traces extending partly on top of the chip 10 (along axis y) and through the chip (along axis z), as necessary to connect to end portions of the lids. The circuit portions 25 join, each, a respective lid 21. The lids 21 can be energized via the electric circuit portions 25, by application of a voltage bias or a current. This allows the lids to be partly dissolved, electrochemically, when they are exposed to an electrochemical solution L (such as an aqueous liquid), as illustrated in FIGS. 4C and 4D. This point is later discussed in detail.

Moreover, masking material portions 22 cover peripheral regions of the lids 21, at the level of the rims 20r, which are in contact with said peripheral regions of the lids. The lids are thus partly recessed under the masking portions 22, as seen in FIGS. 2, 5A-5D, and 6A-6d. This way, the masking portions 22 seal the lids 21, which accordingly seal the cavities. Moreover, the masking portions 22 shield the peripheral regions of the lids from the electrochemical solution L, in operation. Thus, upon electrochemical dissolution of a lid 21 (or part thereof), the electrical circuit portions 25 remain protected from electrochemical dissolution by virtue of the masking portions 22. Without the masking portions 22, the integrity and function of the electrical circuit portions 25 cannot be maintained reliably during the dissolution of a respective lid 21. Hence, the masking portions 22 permit a dissolution of lids 21 with good reproducibility from one cavity 20 to another cavity within an array of cavities.

The rims 20r can be regarded as flanges delimiting the cavities 20. The rims are constituted by portions of the surface S that are in the immediate vicinity of the cavities. I.e., such cavities would be open on said surface S if the lids 21 were not present (the cavities 20 opens upon dissolving the lids). In other words, the cavities, once sealed by the lids 21, formed enclosed compartments.

Thanks to the present solution, each of the lids 21 can be electrochemically dissolved (partly) via an electrical circuit, in a programmed manner, by energizing the lids via the electrical circuit portions 25. The circuits 25 may for example have a crossbar architecture, in order to be able to selectively address and dissolve the lids, as discussed later in detail. The masking portions 22 protects the lids 21 (and, possibly, terminal portions of the circuits 15, 25 see FIG. 5A) from the electrochemical solution L. The portions 22 further help in reinforcing the mechanical stability of the lids 21. That is, the masking portions maintain peripheral regions of the lids 21 that tent over the cavities 20.

Figure 5A:
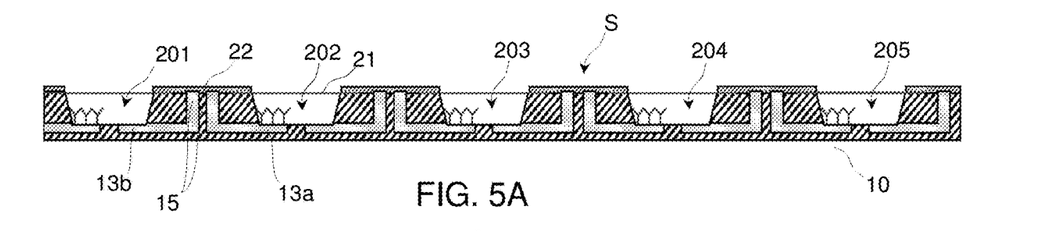
FIGS. 5A-5D show a sequence of 2D cross-sectional views, illustrating how multiple cavities of a same sensor device can be successively exposed for sensing purposes, according to embodiments.
Figure 5B:
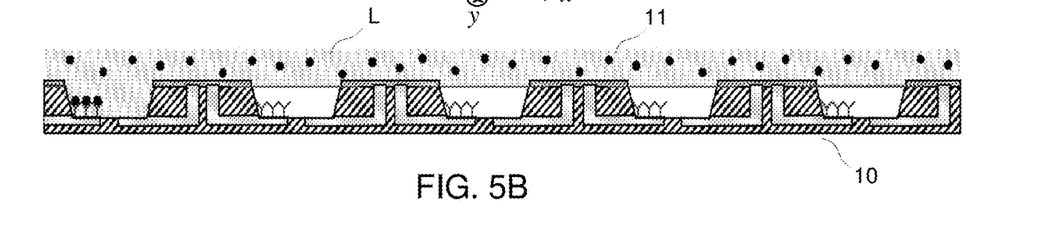
Figure 5C:
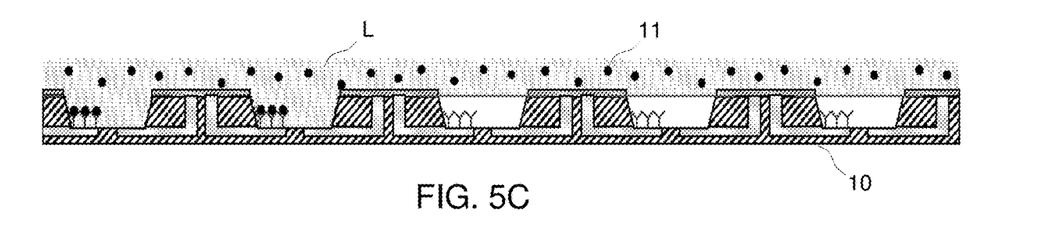
Figure 5D:
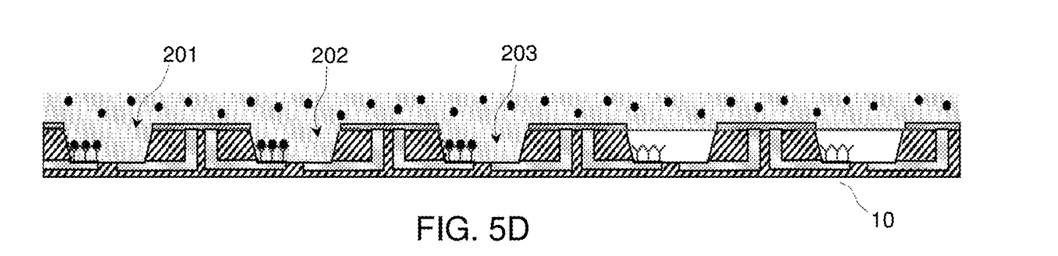

All this is now described in detail, in reference to particular embodiments of the invention. To start with, some of the masking material portions 22 may cover peripheral regions of two neighboring lids 21, as seen in FIG. 5A. Namely, neighboring lids 21 may close respective cavities 20, or sets of cavities that extend along axis y in FIGS. 5A-5D. Such lids 21 may further contact, each, an intermediate portion of the surface S, extending (again along axis y) between two cavities (or sets of cavities, see FIG. 3A). This intermediate portion of the surface S forms rims delimiting neighboring cavities, see FIG. 5A. Then, a masking portion 22 may cover opposite, peripheral regions of two neighboring lids 21, at the level of an intermediate portion of the surface S. Thus, two neighboring lids 21 may be partly recessed under a same masking portion 22, yet without contacting each other, as seen in FIG. 5A. Thus, neighboring lids are physically and electrically separated at the level of a masking portion, to avoid electrical shortcuts and thus make it possible to individually control the electrochemical dissolution of each lid.

As said earlier the present sensors are preferably embodied as biosensors. For example, referring to FIGS. 2, 4A-4D, and 5A-5D, the sensing components of a cavity 20 preferably comprise an electrode 13a arranged in that cavity. The electrode 13a may simply be patterned on a wall (a bottom and/or a lateral wall) of a cavity or be made flush with said wall, thanks to known patterning methods (e.g., based on chemical etching and metal deposition, for example).

Figure 2:
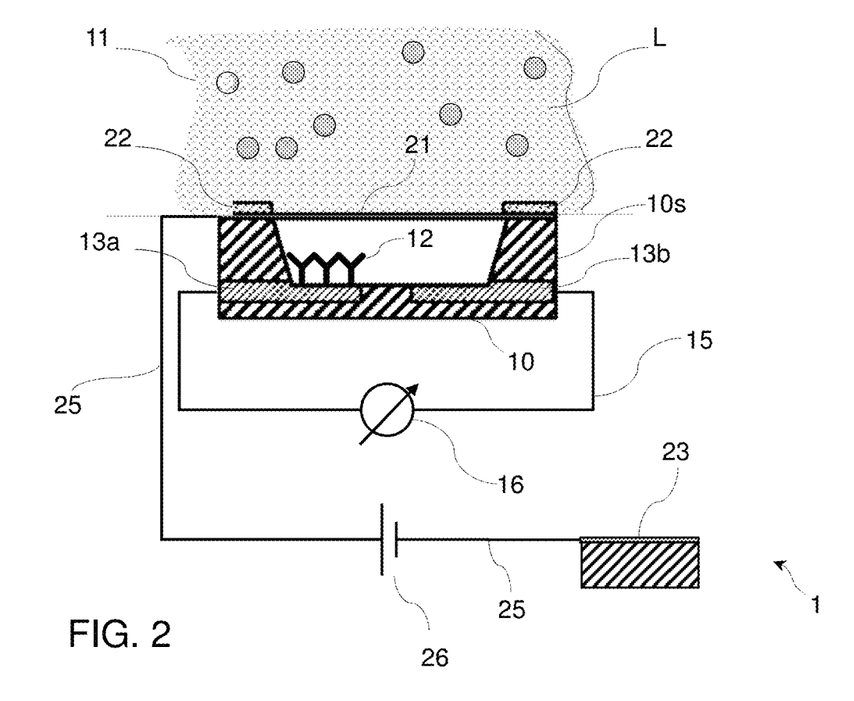
FIG. 2 is a 2D cross-sectional view of a device, which comprises a lid that can be electrochemically dissolved when exposed to an electrochemical solution, to expose the underlying cavity, according to embodiments. Only one such cavity and corresponding lid are shown, for simplicity.

Next, the sensor 1 may include second electric circuit portions 15, distinct from the first electric circuit portions 25. The electric circuit portions may again be formed as electrical traces extending partly on top of the chip 10 (along axis y) and through the chip (along axis z), as necessary to connect to end portions of the electrodes 13a, 13b, as schematically illustrated in FIG. 2. Note, a naked electrode 13a may already be used to perform measurement and sense a liquid. However, the sensing components preferably comprise receptors 12 anchored to said electrode 13a.

The receptors 12 may for example be bioreceptors, as assumed in the accompanying drawings and in the following description, for the sake of exemplification, thus making the sensor 1 a biosensor. The bioreceptors 12 are protected from external media (fluids, humidity, light, etc.) thanks to the lids 21, which seal the cavities (enclosed compartments), see FIG. 4A. After exposure to an electrochemical solution L, see FIG. 4B, and as each lid 21 is individually connected to an electrical circuit portion 25, it can be dissolved on-demand (FIG. 4C), which results in opening up the corresponding cavity(ies) and exposing the bioreceptors therein to the external media L. The receptors 12 can thus bind analytes 11, as depicted in FIG. 4D.

As suggested above, each cavity may further comprise one or more additional electrodes 13b (here called second electrodes), arranged therein. The second electrodes 13b may for instance be essentially free of receptors, e.g., to serve as an auxiliary electrode for amperometric sensing measurements or as a reference electrode where potentiometric sensing techniques are relied on. The second electrodes 13b are connected, each, by respective electric circuit portions 15 (i.e., some of the second electric portions). The portions 15 that connect to electrode pairs 13a, 13b may, in turn, be connected to a readout device 16 (for current or voltage) for measurement purposes. Note, said second electric circuit portions 15 are preferably masked, at least partly, by the masking material portions 22, see FIG. 5A, where the upper electrode elements that lead to the end portions of the electrodes 13a, 13b are masked by the upper portions 22.

In variants, the second electrodes 13b may be located outside of the cavities 20. That is, one or more second electrodes may be arranged at any suitable location on the chip 10, so as to come in contact with liquid L, in operation, and thereby allow measurements. In other variants, the second electrodes could be external, and yet electrically connectable to the chip 10, e.g., through electrical vias and contact pads, as usual in the field of microfluidic chips.

In further variants, one or more third electrodes may be arranged within or outside of the cavities (not shown). Such additional electrodes may combine with electrodes 13a and 13b in a same electrical circuit and be arranged so as to contact the same liquid L to form a three-electrode circuit configuration.

While the second electrodes 13b may possibly be located outside of the cavities 20, placing such electrodes 13b in the cavities 20 instead allows a better signal-to-noise ratio (SNR) to be obtained in practice. Also, because electrodes 13b such as depicted in FIG. 2 are local (i.e., close to their respective companion electrodes 13a), the sensing measurements performed will normally be more accurate.

In all cases, once connected to a suitable readout device 16, the electrodes 13a, 13b make it possible to obtain a signal (voltage or current) that is indicative of the presence and/or concentration of an analyte contained within the external media. The circuit 15 is configured to allow independent sensing operations from the opened cavities, i.e., cavities whose lids have been dissolved. That is, one may selectively sense the external medium via the sensing components of the opened cavities.

An external readout device 16 shall typically be used to that aim, which, together with the chip 10, make up an apparatus according to another aspect of the invention. In variants, however, a simple readout device 16 may be integrated directly on the chip 10, to make up a portable apparatus.

The biosensor devices shown in FIGS. 5A-5D, 6A-6D allow different cavities to be opened on demand, using external electrical control, thereby increasing the number of measurements that can be carried out with the same chip. For example, the same biosensing measurement could be carried out on multiple samples over a long period of time with the same chip (FIGS. 5A-5D). In another example (see FIGS. 6A-6D), different biosensing measurements could be carried out on the same sample with the same device, but the types of measurements carried out may depend on the outcome of the previous measurement(s), as discussed later in reference to sensing methods according to the invention.

In embodiments, each lid 21 has a standard redox potential that is between −0.8 V and +1.6 V, with respect to a standard hydrogen electrode (SHE), which can easily be achieved with a configuration such as depicted in FIG. 2.

Figure 3A:
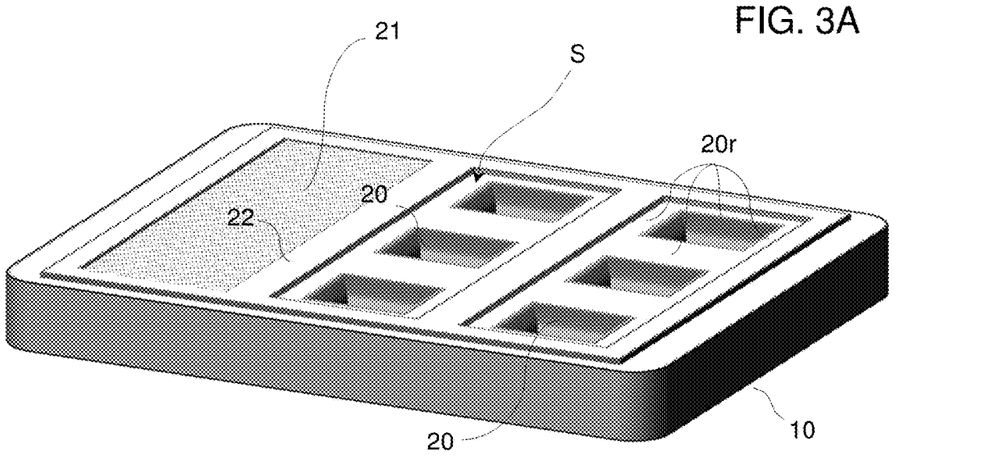
FIG. 3A is a 3-dimensional (3D) view of a sensor device such as shown in FIG. 2, showing multiple cavities arranged in an array, according to embodiments.
Figure 3B:
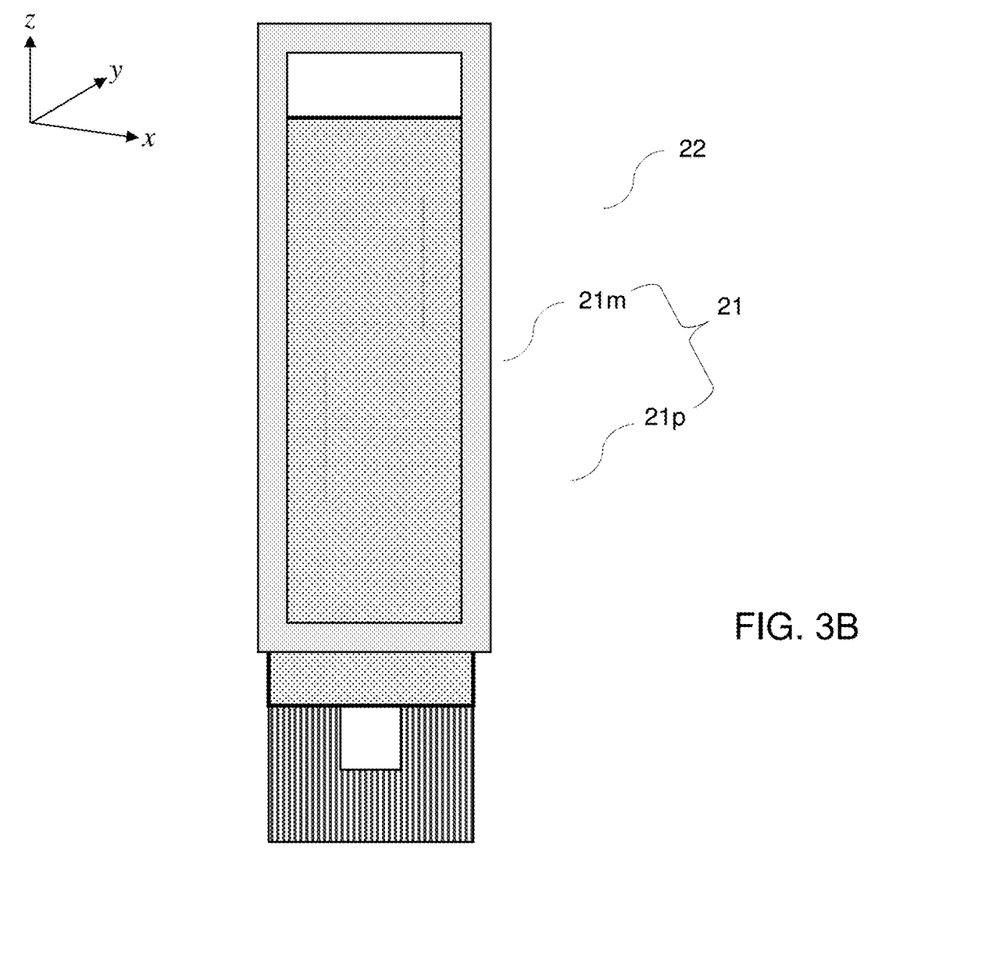
FIG. 3B shows an exploded view of a lid, supported by a reinforcement layer and capped by masking material portions (here structured as a frame), meant to cover peripheral regions of the lid, so as to seal the lid and shield its peripheral regions from an electrochemical solution, according to embodiments.

In the example of FIG. 3B, a lid 21 includes a metallic layer 21m, which may for example comprise gold, silver, aluminum, and/or nickel. In variants, the layers 21m may comprise electrochemically active polymers, such as polypyrrole, polyphenol, which may be electrochemically oxidized by applying appropriate potentials by means of the circuit 25, thereby mechanically breaking apart the lid 21 or making it permeable for the liquid L and/or analyte 11.

The average thickness of the lids 21 shall typically be between 5 and 200 micrometers, to allow an electrochemical dissolution of the lids. Yet, very thin layers of metals or polymers may easily collapse in cavities having an average diameter of 0.1 to 1 or, even, 2 mm as contemplated herein, whence the benefit of using masking portions 22 to reinforce them. That is, the lateral stress induced on the thin foils 21 by the masking portions 22 helps in maintaining the lids 21, for them to neatly tent over the cavities.

Still, as illustrated further seen in FIG. 3B, the lids 21 may further comprise a reinforcement layer 21p of material supporting the metallic layer 21m. I.e., the metallic layer is arranged on top of the reinforcement layer 21p. The latter is structured so as to allow a liquid L to flood the cavities 20 after dissolution of the metallic layer 21m. In addition, or in variants, the cavities 20 may include supporting structures (not shown) arranged in the cavities 20, to help in supporting the lids 21 and prevent the latter from collapsing in the cavities. Depending on the dimensions of the cavities and the thickness of the lids, these additional supporting structures may or may not be needed. For example, no additional supporting structures may be needed if the average diameter of the aperture of the cavities 20 (as measured in the plane (x, y)) does not exceed 0.2 mm, provided that the lids are recessed under the masking portions 22. This, however, depends on the exact thickness adopted for the metal layers 21m.

The chip 10 shall typically be processed from one or two substrates 10s, 10a, which may for example comprise silicon, glass, PDMS, or a ceramic. Such substrates may include stacked layers, as known per se. E.g., an upper layer may be used to process the cavities, while a thicker lower layer could be used to confer the desired mechanical properties. This is discussed later in detail, in reference to FIG. 7

Note, other sensing materials could be used, in variants to the receptors 12. For example, a polymer membrane can be used in place or in addition to the receptors 12, which polymer membrane has a certain affinity to given analytes 11. More generally, other types of sensing techniques could be involved, e.g., relying on optical detection, which may require waveguides arranged in the cavities, as well as a light source and a detector.

Still referring to FIGS. 2-5D, another aspect of the invention is now described, which concerns a sensing apparatus 1. This apparatus involves a sensor that essentially consists of a microfabricated chip 10, which has already been described in detail above, in reference to FIGS. 2-6D. Therefore, this aspect of the apparatus is only briefly recalled in the following. The microfabricated chip 10 includes one or (preferably) more cavities 20 formed on a surface S of the chip 10. As said, the cavities include sensing components 12, 13a, 13b and are closed by lids 21, which contact rims 20r that delimit said cavities on the surface S. Electric circuit portions 25 join respective lids 21 and masking material portions 22 cover peripheral regions of the lids 21 at the level of the rims 20r, so as to seal the lids 21 and shield their peripheral regions, in operation.

Moreover, the apparatus comprises electrical control means 26 (e.g., a voltage and/or a current source), which are connected to said electric circuit portions 25 to allow the lids to be partly dissolved, electrochemically, when exposed to an electrochemical solution L, as explained earlier. Such control means 26 are typically provided in a peripheral.

Consistently with embodiments described earlier, this apparatus is preferably configured as biosensor apparatus. I.e., each cavity 20 may comprise a first electrode 13a arranged therein, with receptors 12 anchored to said first electrodes. Each cavity may possibly comprise a second electrode 13b, for reasons explained earlier, though electrodes 13b may possibly be arranged elsewhere on the chip 10. The chip may comprise second electric circuit portions 15 connected to the first electrodes 13a and second electrodes 13b. In that case, the apparatus 1 may comprise a readout device 16, suitably connected to the electrodes 13a, 13b via the electric circuit portions 15, so as to read measurement signals obtained from the first and second electrodes, in operation.

The sensing apparatus 1 preferably comprises an auxiliary electrode 23 (e.g., made of platinum), which is connected to the electrical control means 26, via a branch of the electrical circuit 25, so as to be in electrical communication with the lids. The control means 26 are configured to apply a voltage bias between a selected one of said lids 21 and the auxiliary electrode 23 (which can therefore be regarded as a counter electrode), to allow the lids 21 to be partly dissolved. The auxiliary electrode 23 can be arranged so as to be exposed to the sensed medium L, to help in achieving the potential required to dissolve the lids. Note, in variants, the control means 26 may be configured to drive a current to thereby dissolve the lid. In the case of controlled current, the electrochemical potential of the lid layer 21m will generally change over time, while in the case of controlled voltage the dissolution current will generally change over time. Both approaches are viable to achieve the desired dissolution of the lid.

One or more auxiliary electrodes 23 may be relied on, depending on the configuration of the circuit 25, 26. I.e., a single electrode 23 may be used, which is in electrical communication with all lids 21 via the control means 26. In variants, each lid 21 may be connected to a respective, auxiliary electrode 23. Note, such auxiliary electrodes 23 are preferably arranged so as to come in contact with the medium L. This, however, is not a strict requirement.

Additional embodiments are now discussed, which concerns possible crossbar architectures for addressing and dissolving selected lids. In a simple approach, a membrane (lid) and respective sensing components form a single cell, which corresponds to a respective cavity. Such cells are placed at intersections of the crossbar structure. An issue with this approach, however, is that increasing the number of cells (array size) results in increasing leakage currents. Moreover, the resistance of the membrane in the target cell increases during the membrane dissolution, which results in driving increasing current into the neighboring cells. Relying on the so-called 1T1R crossbar configuration solves this problem but requires an active switching element for every cell. Two options can be contemplated to achieve this, namely placing the active switching elements (i) on top of the cell or (ii) on the bottom thereof. The first option can notably be achieved by using thin-film electronics on a polymer film, which is applied to the top of the cell array. The membrane is placed so as for the thin film to be opened in the vicinity of the sensors and make them accessible by the fluids to be sensed. For the second option, the sensor cells can for example be manufactured on the backside of a silicon chip, whereby the switched current can be applied to the membranes by means of through-silicon vias.

Referring to FIGS. 3A-5D, a final aspect of the invention is now described, which concerns sensing methods. Such methods rely on a sensor 1 or an apparatus such as described above, see, e.g., FIG. 4A. Essentially, such methods require exposing the surface S of the chip 10 to an electrochemical solution L, FIG. 4B, and energize the electric circuit portions 25 connecting a selected lid 21 to electrochemically dissolve an inner region of this lid, FIG. 4C. This is preferably achieved by applying a voltage bias (e.g., of +2 V) between the selected lid 21 and an auxiliary electrode 23. In practice, the applied voltage bias is approximately equal to or higher than the standard redox potential. For example, a bias of +2 V would be appropriate for standard redox potentials ranging from −0.8 V to +1.6 V.

In variants to applying to potential biases, a current may be applied to achieve the same. In that case, the sign of the applied current is such as to polarize the lid 21 toward a more positive and therefore oxidative potential according to the electrochemical convention.

As noted earlier, the peripheral regions of the lid remain shielded from the electrochemical solution L by the masking portions 22. This results in exposing the sensing component(s) 12, 13a, 13b of the corresponding cavity(ies) to an external medium L. Eventually, this external medium (or particles therein) is sensed via the sensing components 12, 13a, 13b, FIG. 4D, based on principles as described earlier. The above steps can be performed for several lids together, or one at a time (successively), etc.

In particular, the electrochemical solution L used to dissolve the lid(s) may already contain analytes 11 to be subsequently sensed. Thus, the electrochemical dissolution of the lid(s) may cause to directly expose the sensing components 12, 13a, 13b to such analytes 11, which can subsequently be sensed. Note, the dissolution and sensing steps may be partly concomitant, to accelerate the process.

As said, the cavities 20 preferably comprise electrodes 13a, 13b, wherein receptors 12 for said analytes 11 are anchored to one 13a of the electrodes 13a. Thus, analytes 11 can be sensed via a measurement signal obtained thanks to the electrodes 13a, 13b. That is, upon dissolving the lid (FIG. 4C), the liquid sample L floods the cavity 20 and analytes 11 binds to bioreceptor 12, which generates a measurable signal (FIG. 4D).

The above steps can be repeated over time, e.g., to perform multiple measurements (with the same chip 10), by successively selecting different cavities, as illustrated in FIGS. 5A-5D. Note, FIGS. 5B-5D capture a measurement sequence that could be performed with samples taken from a same individual or from different individuals at different times, without unnecessarily degrading or contaminating bioreceptors contained in the cavities.

In the variant of FIGS. 6A-6D, the outcome of the last measurement(s) impacts the selection of the next cavity, which may include distinct receptors or a larger (number of) electrodes 13a (thus with a larger quantity of receptors), should a confirmation be needed, or the SNR be improved. Preferred, however, is to have subsets of cavities filled with distinct types of receptors 121-125, so as to be able to sense distinct analytes 111-113, as assumed in FIGS. 6A-6D.

Thus, after having exposed the chip to a liquid L (FIGS. 6A-6B) and opened a given cavity 202 (by dissolving a corresponding lid 212) to sense first analytes 111 (FIG. 6B), additional lids 214, 215 may be selected based on an outcome of a previous sensing step, or based on outcomes of multiple previous steps, depending on the protocol adopted. Then, the selected lids may be electrochemically dissolved, in order to expose receptors 124, 125 to analytes 111-113 in an electrochemical solution L. Note, depending on the experiment, this solution L may be identical to the previous solution, or not. The chip 10 may possibly remain exposed to the same liquid sample L, or not. Finally, analytes 111-113 of the solution L can be similarly sensed, via measurement signals obtained thanks to electrodes 13a, 13b of the latest opened cavities, FIG. 6C. Note, in this example, analytes 112 happen to bind to receptors 125, while no analyte binds to receptors 124. The same principle can be repeated once, which causes to open up a further cavity, and so on.

Figure 6A:
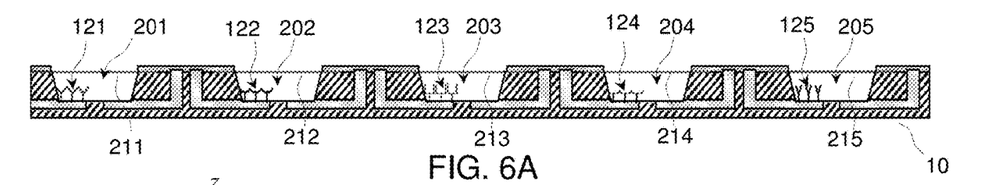
FIGS. 6A-6D show a further sequence, which illustrates how cavities of a same sensor device can be programmatically exposed, based on outcomes of previous sensing steps, for sensing different analytes, according to embodiments.
Figure 6B:
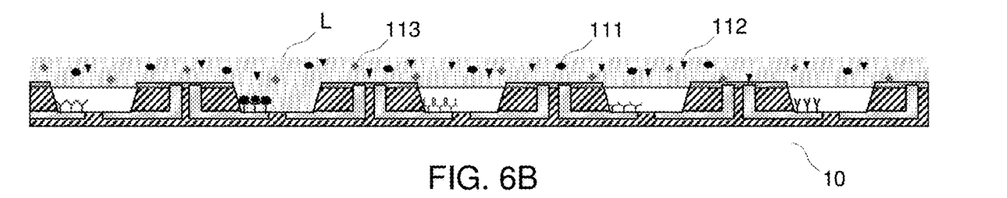
Figure 6C:
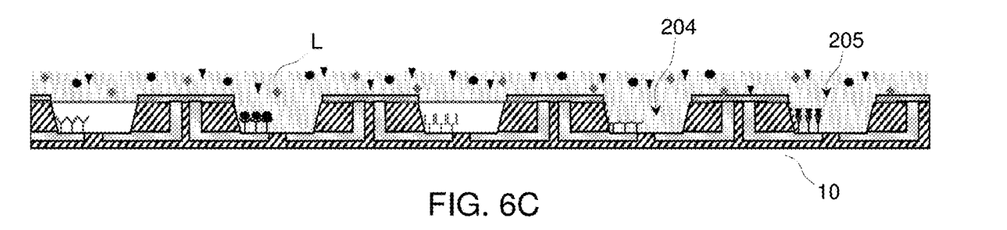
Figure 6D:
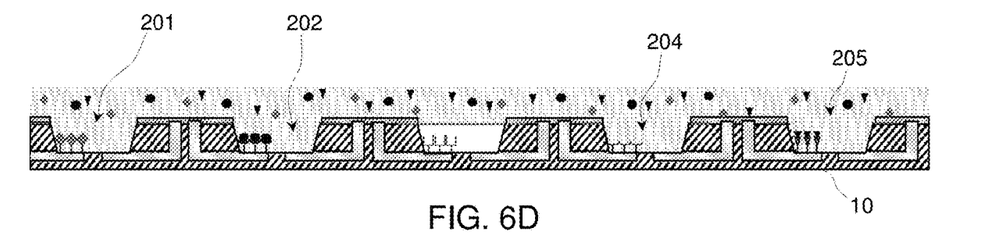

In detail, the scenario assumed in FIGS. 6A-6D is the following: A positive response from the cavity 202 (FIG. 6B) triggers further tests, whereby cavities 204, 205 are opened (FIG. 6C). Now, only the signal sensed from cavity 205 provides a positive response. This, in turn, triggers another specific test, whereby a final test is performed in cavity 201, which provides a positive response. Eventually, a comprehensive dataset is obtained, e.g., for diagnosis purposes.

Figure 7:
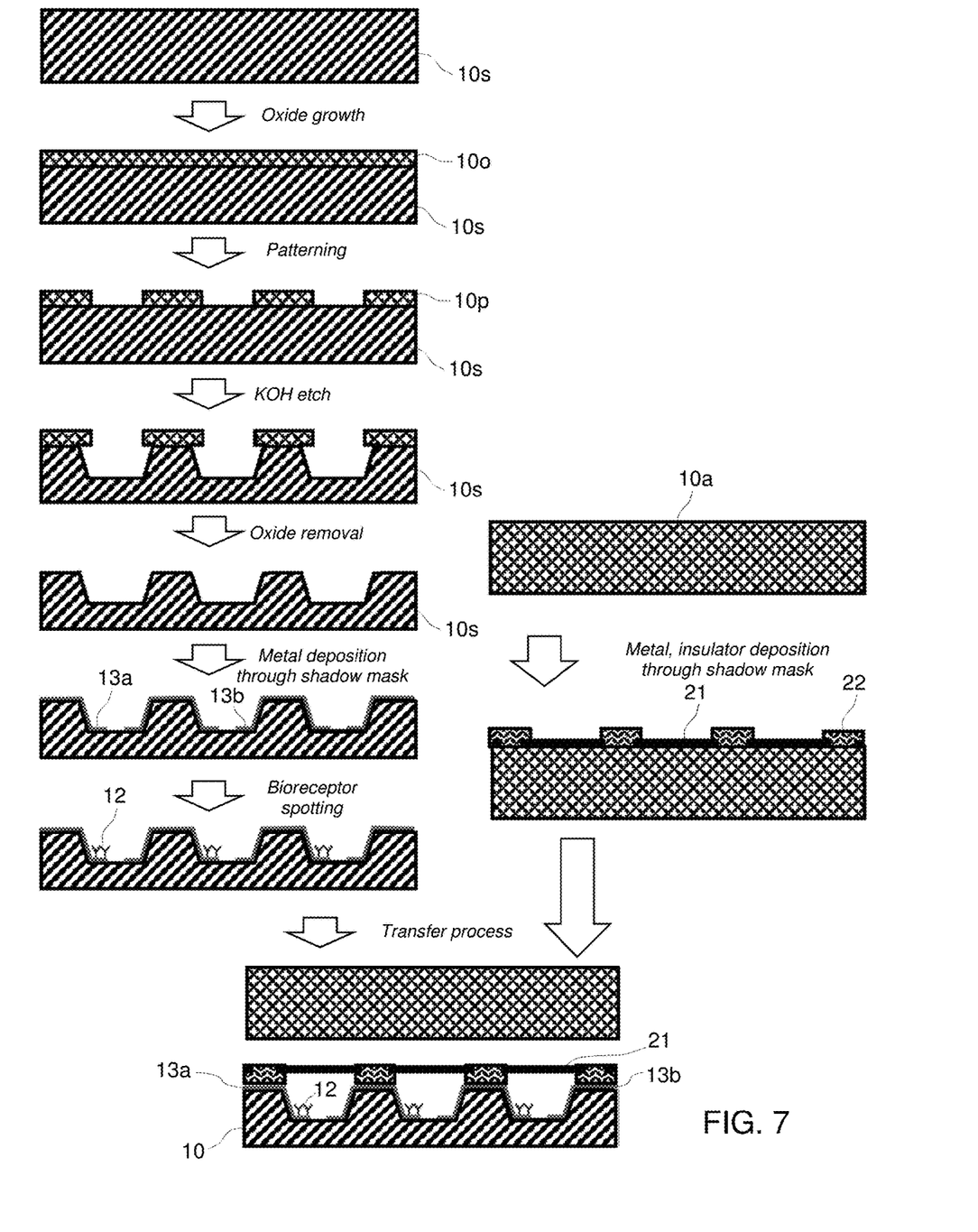
FIG. 7 is another sequence of 2D cross-sectional views illustrating high-level fabrication steps of a sensor device according to embodiments.

The peripherals 16, 26 used for dissolution control and readout purposes are known per se. The chip 10 can notably be fabricated as follows. As seen in FIG. 7, a silicon substrate 10s may for example be provided, which is oxidized to yield a superficial oxide layer 10o. The latter is subsequently patterned, resulting in a crenellated pattern 10p. A subsequent etching step (using KOH) results in forming cavities in the substrate 10s. The residual oxide is then removed, and a metallic layer is deposited through a shadow mask, to pattern electrodes 13a, 13b, before spotting the receptors 12. Next, another substrate 10a (e.g., comprising silicon or PDMS) is patterned, similarly to the structure 10s, 10p, and a metal layer is deposited (again, through a shadow mask) to obtain neighboring metal lids 21, before the transfer process. Care is taken to make sure that residual masking portions 22 protrude above and cover peripheral regions of the lids 21. Variants to the above process can be contemplated, possibly involving other materials, as the one skilled in the art will appreciate.

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated. For example, a preferred electrochemical biosensor is one that comprises one or more cavities (or compartments) provided within or on a support, where lids (or membranes) separates inner spaces of said compartments from an external medium, which prevents fluid communication with the inner spaces of said compartments. This membrane is electrically connected to a first electrical circuit which comprises a voltage and current source and an auxiliary electrode, and it has the property of dissolving in aqueous liquids upon application of a positive potential with respect to said auxiliary electrode. One or more measurement electrodes are located within the compartments, wherein the surface of at least one of the measurement electrodes is covered by bioreceptors. The measurement electrodes are electrically connected to a second electrical circuit which comprises a readout device (for voltage or current). Moreover, the present devices may possibly include various microstructures such as flow paths (e.g., subtended by microchannels and other structures), capillary pumps, vents, contact pads, etc., as known in the art.

What is claimed is:

1. A sensor comprising:
    a microfabricated chip having a surface with one or more cavities formed thereon, the cavities including sensing components;
    one or more lids, each covering said surface so as to close at least one of said cavities, the lids contacting rims that delimit said cavities on said surface;
    electric circuit portions, each joining a respective one of the lids, configured to allow the lids to be at least partly dissolved, electrochemically, responsive to being exposed to an electrochemical solution;
    and masking material portions covering peripheral regions of the lids at the level of the rims, so the masking material portions are configured to seal the lids and shield such peripheral regions from said electrochemical solution, in operation.

2. The sensor according to claim 1, wherein
    said one or more lids include two neighboring lids, which close respective ones of said cavities and contact, each, an intermediate portion of the surface, which forms rims delimiting said respective ones of said cavities, and said masking material portions covers peripheral regions of the two neighboring lids at the level of this intermediate portion of the surface.

3. The sensor according to claim 1, wherein the sensing components comprise, each,
an electrode arranged in a respective one of the cavities, and
receptors anchored to said electrode, and said electric circuit portions are first electric circuit portions, the sensor including second electric circuit portions connected to said electrode.

4. The sensor according to claim 3, wherein said electrode is patterned on a wall of the respective cavity.

5. The sensor according to claim 3, wherein said electrode is a first electrode, and the cavities comprise, each, a second electrode arranged therein, wherein said second electrode is connected by the second electric circuit portions.

6. The sensor according to claim 3, wherein said masking material portions at least partly mask said second electric circuit portions.

7. The sensor according to claim 3, wherein each of the lids has a standard redox potential between −0.8 V and +1.6 V with respect to a standard hydrogen electrode.

8. The sensor according to claim 7, wherein each of the lids includes a metallic layer that essentially comprises one or more of the following metals: gold, silver, aluminum, and nickel.

9. The sensor according to claim 8, wherein each of the lids further comprises a reinforcement layer of material supporting said metallic layer, the latter arranged on top of the reinforcement layer, which is structured so as to allow a liquid to penetrate the cavities upon dissolution of the metallic layer.

10. The sensor according to claim 1, wherein an average diameter of an aperture of the cavities at the level of said surface is less than 1.0 mm.

11. The sensor according to claim 1, wherein an average thickness of said lids is between 5 and 200 micrometers.

12. A sensing apparatus, comprising:
a microfabricated chip, wherein the chip includes:
a surface with one or more cavities formed thereon, the cavities including sensing components;
one or more lids, each covering said surface so as to close at least one of said cavities, the lids contacting rims that delimit said cavities on said surface;
electric circuit portions, each joining a respective one of the lids; and
masking material portions covering peripheral regions of the lids at the level of the rims so the masking material portions are configured to seal the lids and shield said peripheral regions from said electrochemical solution, in operation;
and an electrical control, connected to said electric circuit portions, and configured to allow the lids to be at least partly dissolved, electrochemically, responsive to being exposed to an electrochemical solution.

13. The sensing apparatus according to claim 12, wherein the cavities comprise first electrodes respectively arranged therein, wherein receptors are anchored to said first electrodes, the apparatus further comprises one or more second electrodes, said electric circuit portions are first electric circuit portions, the chip comprising second electric circuit portions connected to said first electrodes and second electrodes, and the apparatus further comprises a readout device, the latter configured to read measurement signals obtained from the first and second electrodes via the electric circuit portions, in operation.

14. The sensing apparatus according to claim 13, wherein the apparatus further comprises an auxiliary electrode, and said electrical control means are further connected to said auxiliary electrode, the electrical control means configured to apply a voltage bias between a selected one of said lids and said auxiliary electrode, to allow the lids to be partly dissolved.

15. A sensing method comprising:
providing a sensor, the latter including:
a microfabricated chip having a surface with one or more cavities formed thereon, the cavities including sensing components;
one or more lids, each covering said surface so as to close at least one of said cavities, the lids contacting rims that delimit said cavities on said surface;
electric circuit portions, each joining a respective one of the lids; and
masking material portions covering peripheral regions of the lids at the level of the rims;
exposing the surface of the chip to an electrochemical solution;
energizing the electric circuit portions connecting one of the lids to electrochemically dissolve an inner region thereof, its peripheral regions being shielded from said electrochemical solution by one or more of the masking portions, in order to expose one or more of the sensing components to an external medium; and
sensing said external medium via said one or more of the sensing components exposed.

16. The method according to claim 15, wherein energizing said electric circuit portions causes said sensing components to be exposed to analytes contained in said electrochemical solution upon, whereby sensing said external medium comprises sensing said analytes.

17. The method according to claim 16, wherein the cavities of the sensor provided comprise first electrodes respectively arranged therein, wherein receptors for said analytes are anchored to said first electrodes, the sensor comprising one or more second electrodes arranged so as to come in contact with said external medium, in operation, and sensing said external medium comprises sensing analytes of said external medium via a measurement signal obtained thanks to: the first electrode arranged in one of the cavities corresponding to said one of the lids; and one or more of the second electrodes.

18. The method according to claim 17, wherein the method further comprises:
selecting another one of the lids, based on an outcome of the sensing of said analytes;
energizing the electric circuit portions connecting the selected lid to electrochemically dissolve an inner region thereof as the surface of the chip is exposed to an electrochemical solution, whereas peripheral regions of the selected lid are shielded from the electrochemical solution by one or more of the masking portions, in order to expose receptors of one or more cavities corresponding to the selected lid to analytes in an electrochemical solution; and sensing analytes in said another electrochemical solution via a measurement signal obtained thanks to: one of the first electrodes that is arranged in a cavity corresponding to the selected lid; and one or more of the second electrodes.

19. The method according to claim 18, wherein receptors in the cavity corresponding to said selected lid differ from receptors in the cavity corresponding to said one of the lids, so as to sense distinct analytes.

20. The method according to claim 15, wherein said electric circuit portions are energized by applying a voltage bias between selected one or more of said lids and an auxiliary electrode.

* * * * *